(12) United States Patent
Laghi et al.

(10) Patent No.: US 12,295,723 B2
(45) Date of Patent: May 13, 2025

(54) APPARATUS FOR VOLUME MANAGEMENT OF RESIDUAL LIMB

(71) Applicants: Alps South Europe, s.r.o., Plzen (CZ); Aldo Laghi, Pinellas Park, FL (US)

(72) Inventors: Aldo Laghi, Pinellas Park, FL (US); Nathaniel Vint, Pam Harbor, FL (US)

(73) Assignee: Alps South, LLC, St. Petersburg, FL (US)

( * ) Notice: Subject to any disclaimer, the term of this patent is extended or adjusted under 35 U.S.C. 154(b) by 751 days.

(21) Appl. No.: 17/501,554

(22) Filed: Oct. 14, 2021

(65) Prior Publication Data

US 2022/0110544 A1    Apr. 14, 2022

Related U.S. Application Data

(60) Provisional application No. 63/091,347, filed on Oct. 14, 2020.

(51) Int. Cl.
| | | |
|---|---|---|
| *A61B 5/107* | (2006.01) | |
| *A61B 5/00* | (2006.01) | |
| *A61F 2/78* | (2006.01) | |
| *A61F 2/80* | (2006.01) | |

(52) U.S. Cl.
CPC .......... *A61B 5/1073* (2013.01); *A61B 5/4878* (2013.01); *A61B 5/6811* (2013.01); *A61F 2/80* (2013.01); *A61F 2002/7818* (2013.01)

(58) Field of Classification Search
CPC ..... A61B 5/107; A61B 5/1072; A61B 5/1073; A61B 5/6804; A61F 2/76; A61F 2/78; A61F 2/80; A61F 2/5046; A61F 2002/5083; A61F 2002/7615; A61F 2/50; A61F 2002/7818; A41H 1/02; Y10S 623/901

See application file for complete search history.

(56) References Cited

U.S. PATENT DOCUMENTS

| | | | |
|---|---|---|---|
| 2,112,930 A * | 4/1938 | Shulman | A41H 1/02 |
| | | | D10/62 |
| 2,202,598 A | 5/1940 | Peterson | |
| 7,356,379 B2 * | 4/2008 | Slemker | A61F 2/5046 |
| | | | 700/118 |
| 2007/0162153 A1 | 7/2007 | Barnes | |
| 2017/0105853 A1 * | 4/2017 | Jonsson | A61F 2/80 |

* cited by examiner

*Primary Examiner* — David J. McCrosky
(74) *Attorney, Agent, or Firm* — Cole Carlson

(57) ABSTRACT

An apparatus for residual limb volume management. Specifically the present invention relates to tapered prosthetic socks used in combination with a measuring template such that, when compressed, a user can see whether or not their residual limb has swelled or shrunk. The point at which the top edge of the socket of the prosthetic stops when in a compressed stance is the "0" mark on the measuring template and any upward or downward movement will be noticed by the user via a baseline drawn onto the prosthetic sock made using the measuring template. A mobile/online application can be implemented to remind the user to regularly check the baseline and instruct the user if corrective action is needed.

3 Claims, 6 Drawing Sheets

APPARATUS FOR VOLUME MANAGEMENT OF RESIDUAL LIMB

TECHNICAL FIELD

This disclosure relates to volume management of a residual limb. More specifically, this disclosure relates to an apparatus that allows a user to measure a residual limb's volume change due to a variety of factors through the use a tapered prosthetic sock in combination with visual detection of volume change.

BACKGROUND OF THE INVENTION

Over time the volume of an amputee's residual limb can change due to a variety of reasons. These reasons include change in ambient temperature, water retention, a woman's menstrual cycle, change in diet, use of diuretics, diabetes, or simply age. As the volume of the residual limb changes, the fit of the prosthetic socket is compromised which can, in turn, lead to loss of control of the prosthetic limb.

Current methods of volume management for residual limbs use prosthetic socks which exhibit a constant wall thickness from the distal end to the proximal end. Some socks also feature a tapered orientation from the distal end to proximal end. For example, a sock currently in use and offered by Ottobock® is cylindrical in shape and thick distally (3 ply) and thin proximally (1 ply) for use with cushion liners. The issue with this sock is a lack of effectiveness for volume management control due to varying thickness when stretched over the residual limb. A residual limb can shrink or swell at different rates proximally and distally depending on the ratio of muscle and fat to bone. Ideally, a prosthetic would have a tapered thickness having a thicker distal end and thinner proximal end for below knee amputees or, instead, a thinner distal end and thicker proximal end for above knee amputees. There is also a requirement for below knee amputees for loading where it may not be advisable to add thickness at the distal end as it would upset the loading requirement of ⅓ distal end thickness to ⅔ circumferential thickness. Tapered prosthetic socks have been patented previously but make no mention of the option of having the distal end be 1 ply. Examples include U.S. Pat. No. 2,202,598 to Peterson and U.S. Publication No. 2007/0162153 to Barnes et al. Further, some amputees lack sensory perception in the residual limb due to vascular deficiencies or diabetes such that they may not sense a change in limb volume or prosthetic use until it becomes a major problem.

The present invention overcomes the aforementioned inadequacies of the prior art and current need in the industry by using unique tapered prosthetic socks in combination with a template to mark where the prosthetic should sit when in a compression stance and an application which informs the user of which ply sock to use if there has been swelling or shrinkage of the residual limb.

Therefore, it is an object of this invention to provide an improvement which overcomes the aforementioned inadequacies of the prior art devices and provides an improvement which is a significant contribution to the advancement of residual limb volume management art.

Another object of the invention is to provide tapered prosthetic socks which allows an amputee to estimate the thickness needed to be added or removed to the prosthetic sock so as to provide proper volume management under compression.

Another object of the invention is to provide an online or mobile application which can educate or remind the patient about how to check for residual limb volume change, when to check for residual limb volume changes, how to read the position of the prosthetic sock, and how to correct for volume changes as well as provide the amputee with the correct ply of sock to use in case of volume change.

Another object of the invention is to educate and inform users about different plies of yarn and knit construction to create different compressed thicknesses.

Another object of the invention is to provide a visual alert to a user that the volume of their residual limb has changed.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The present invention relates generally to an apparatus for residual limb volume management. Specifically the present invention relates to tapered prosthetic socks used in combination with a measuring template such that, when compressed, a user can see whether or not their residual limb has swelled or shrunk. The point at which the top edge of the socket of the prosthetic stops when in a compressed stance is the "0" mark on the measuring template and any upward or downward movement will be noticed by the user via a baseline drawn onto the prosthetic sock made using the measuring template. A mobile/online application can be implemented to remind the user to regularly check the baseline and instruct the user if corrective action is needed.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which.

Similar reference numerals refer to similar parts throughout the several views of the drawings.

DETAILED DESCRIPTION OF THE DRAWINGS

The following description is of the best mode presently contemplated for carrying out the invention. This description is not to be taken in a limiting sense, but is made merely for the purpose of describing one or more preferred embodiments of the invention. The various components of the present invention, and the manner in which they interrelate, are described in greater detail hereinafter. The scope of the invention should be determined with reference to the claims.

Figure 1:
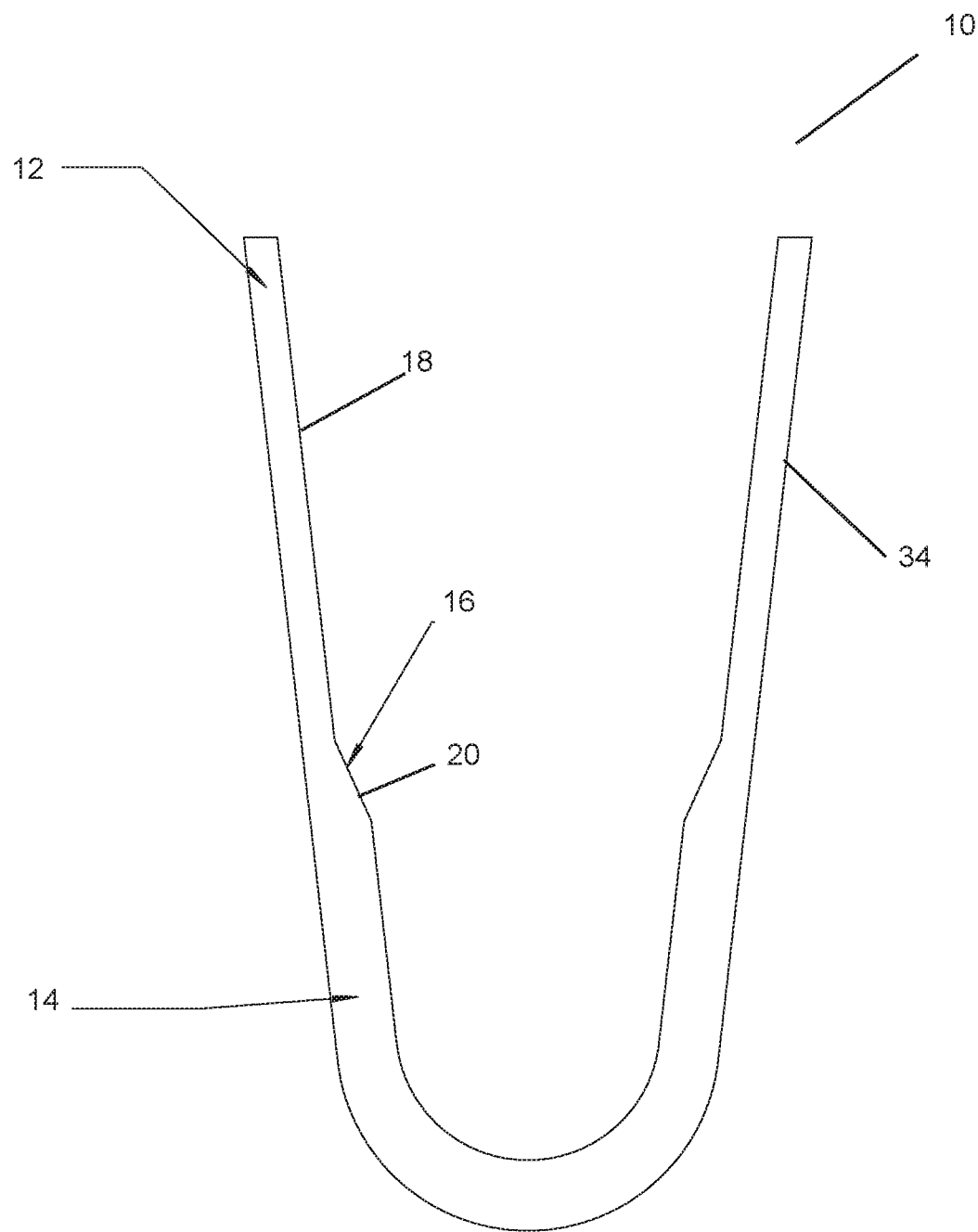
FIG. 1 is a cross-sectional view of a prosthetic sock to be used with below-the-knee amputees for the present invention.
Figure 2:
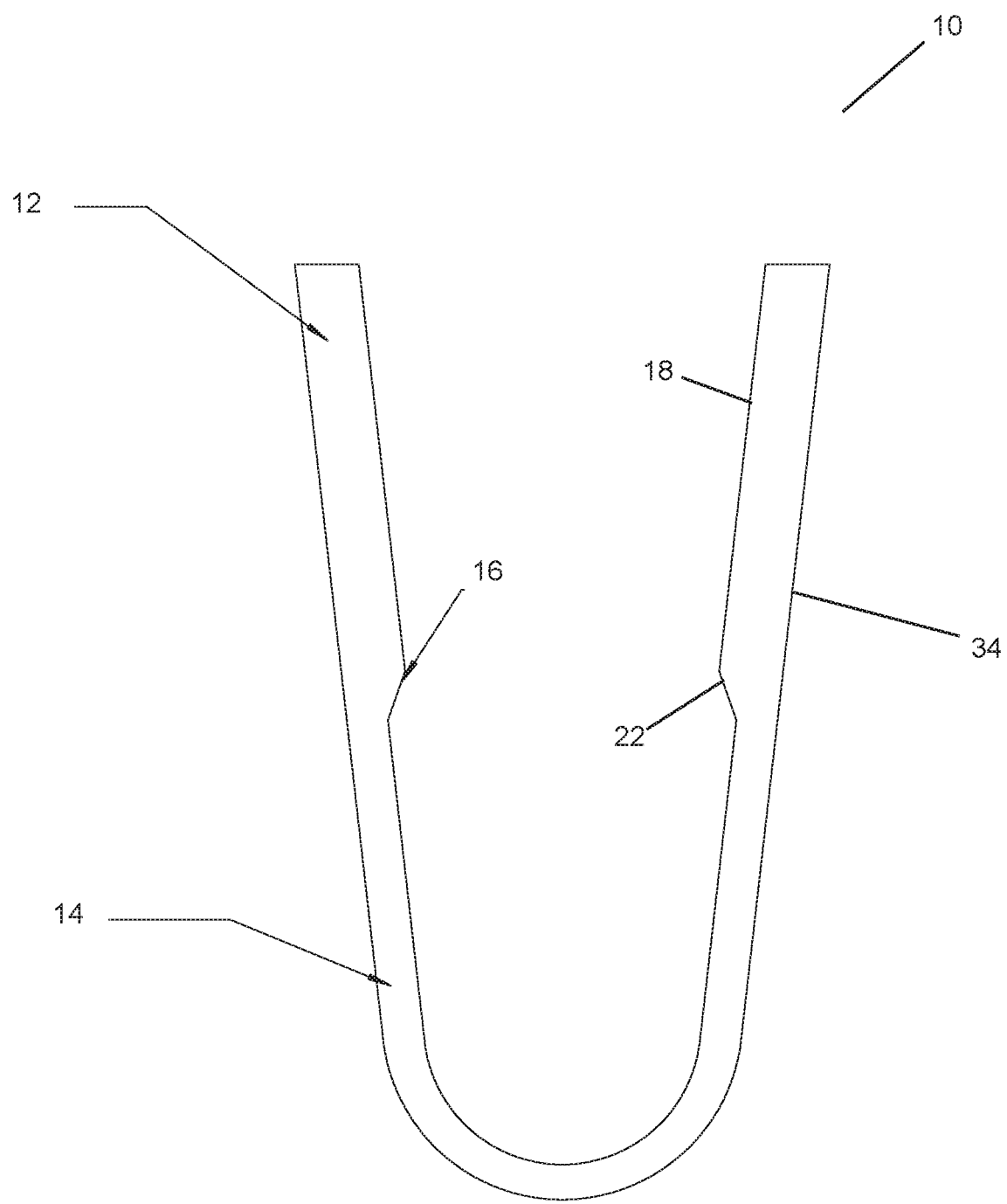
FIG. 2 is a cross-sectional view of the prosthetic sock to be used with above-the-knee amputees for the present invention.

The present invention relates to a prosthetic sock 10 for use with prosthetic or orthotic devices. As shown in FIG. 1, the prosthetic sock 10 generally used for below-the-knee amputees can be thinner at the proximal end 12 than at the distal end 14 with a transition line 16 providing the point at which the inner surface 18 begins increasing in thickness forming a inwardly taper 20. The proximal end 12 has a thickness between 0.4 to 1.0 millimeters. The distal end 14 has a thickness between 1.2 to 1.8 millimeters. Likewise, as shown in FIG. 2, the prosthetic sock 10 generally used for above-the-knee amputees can be thinner at the distal end 14 than at the proximal end 12 with the transition line 16 providing the point at which the inner surface 18 begins decreasing in thickness forming an outward taper 22. The prosthetic sock 10 of FIG. 2 has a thickness of between 0.4 and 1.0 millimeters at the distal end 14 and 1.2 to 1.8 millimeters at the proximal end 12.

Figure 3:
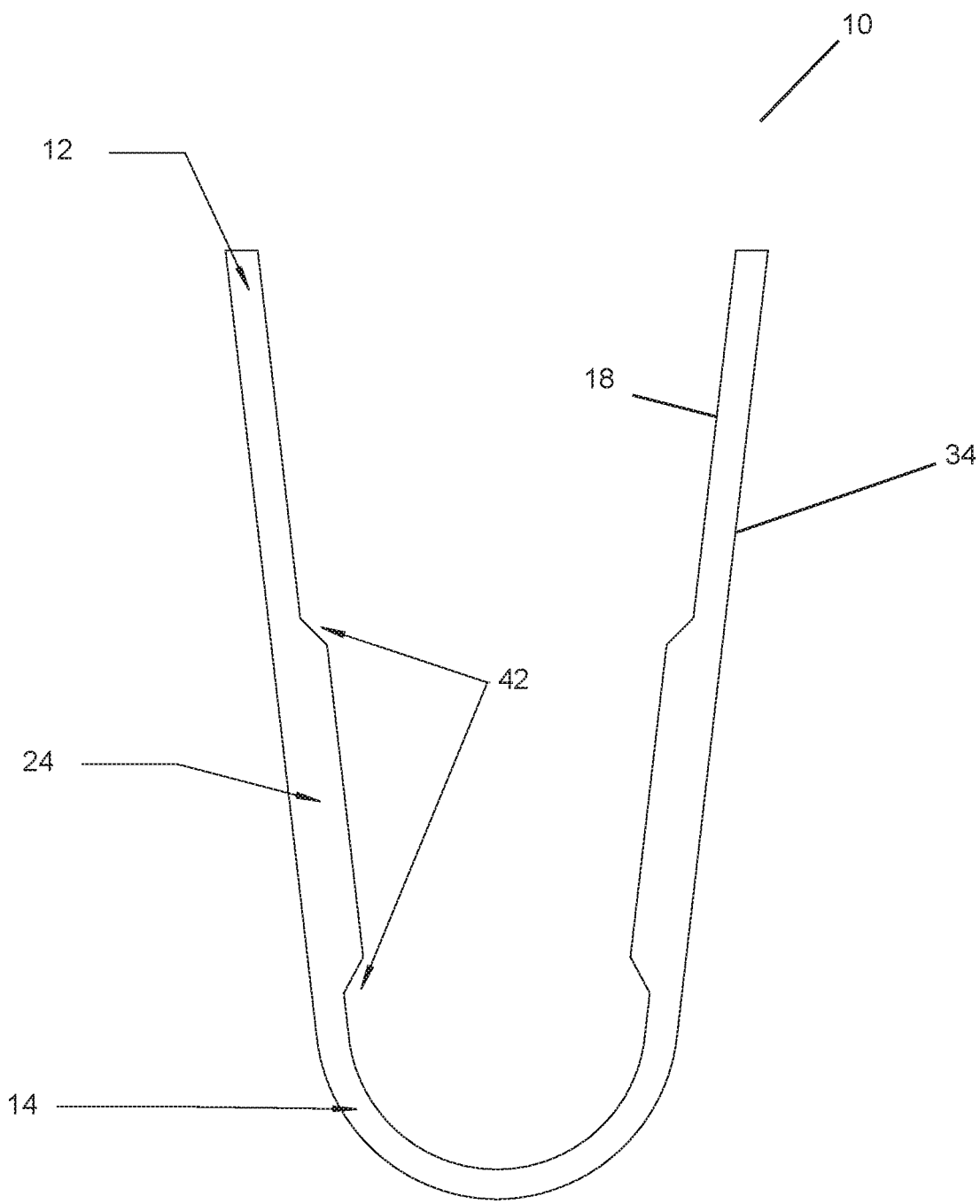
FIG. 3 is a cross-sectional view of the prosthetic sock to be used in situations where the loading requirement should not be upset for the present invention.

As seen in FIG. 3, there may be a situation where a below-the-knee amputee requires a different set-up so as to maintain a proper loading requirement. In this situation the prosthetic sock 10 can taper inward from the proximal end 12 in the medial section 24 and then taper back outward towards the distal end 14 forming medial transition lines 42. This medial section 24 has a thickness between 1.2 and 1.8 millimeters whereas the proximal end 12 and distal end 14 preferably have thicknesses between 0.4 and 1.0 millimeters.

Figure 4:
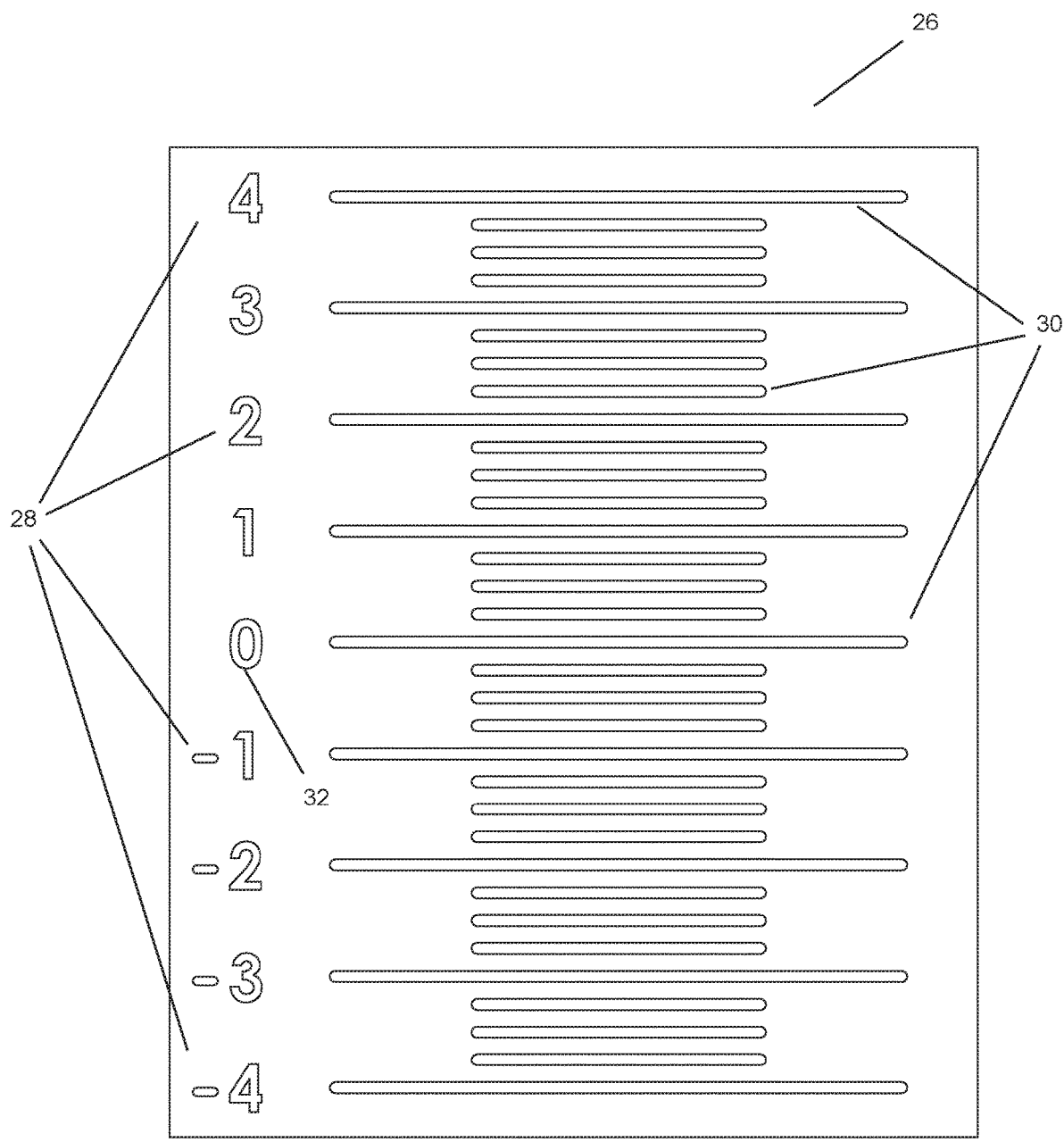
FIG. 4 is a front perspective view of the measuring template.

As seen in FIG. 4, the measuring template 26 has a plurality of height indicators 28 as well as a plurality of measurement spaces 30 spaced evenly across the measuring template 26. Preferable the height indicators 28 are spaced one inch apart from one another. Important to note is the zero mark 32 which serves as the baseline for the prosthetic sock 10 when initially being measured for the amputee. As shown, the measuring template 26 goes four inches above and below the zero mark 32 but this should not be taken as limiting in terms of how far from the zero mark 32 the measuring template 26 could go.

Figure 5:
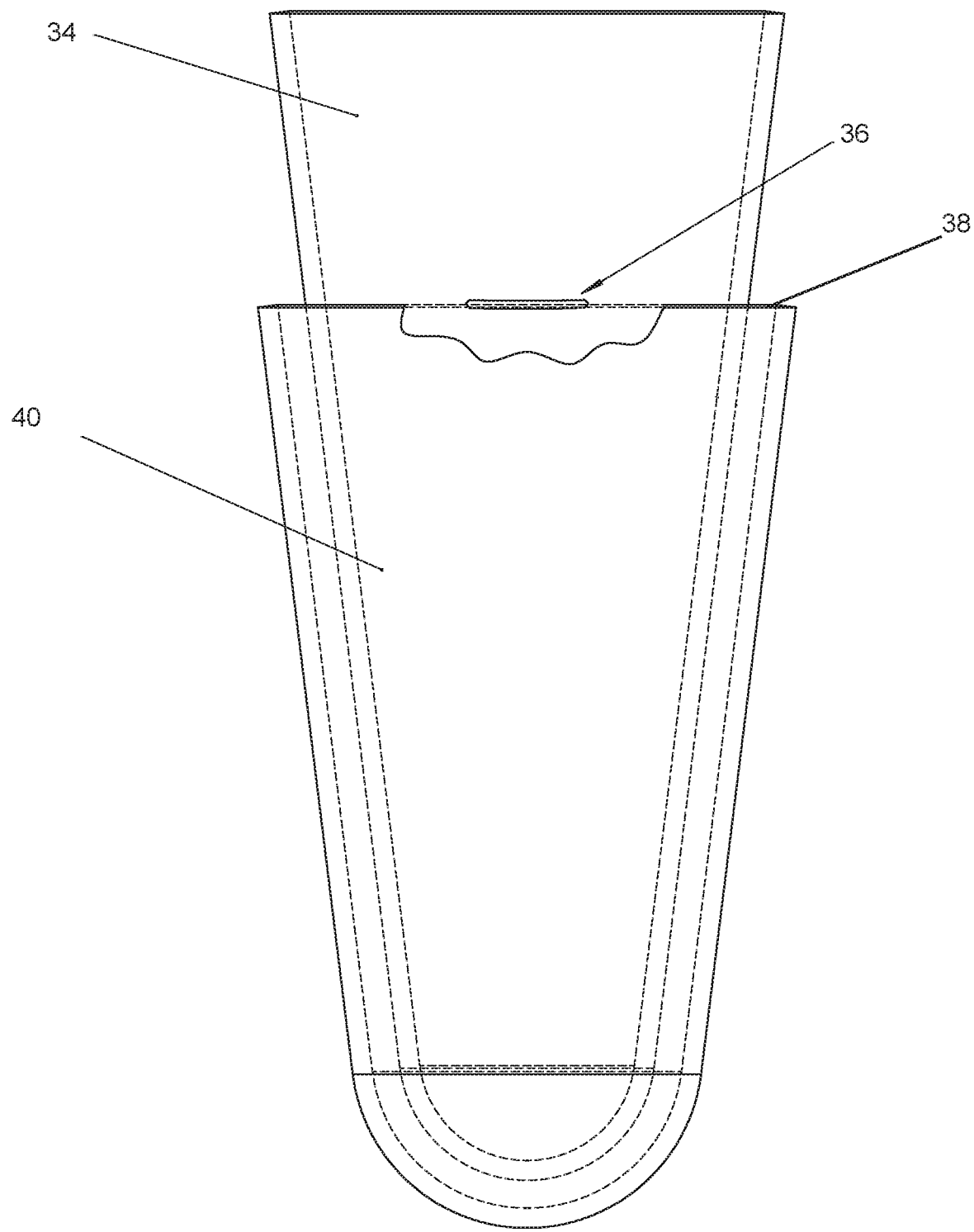
FIG. 5 is a view of the prosthetic sock of the present invention in combination with a prosthetic socket with a cutout to show the baseline drawn onto the prosthetic sock.
Figure 6:
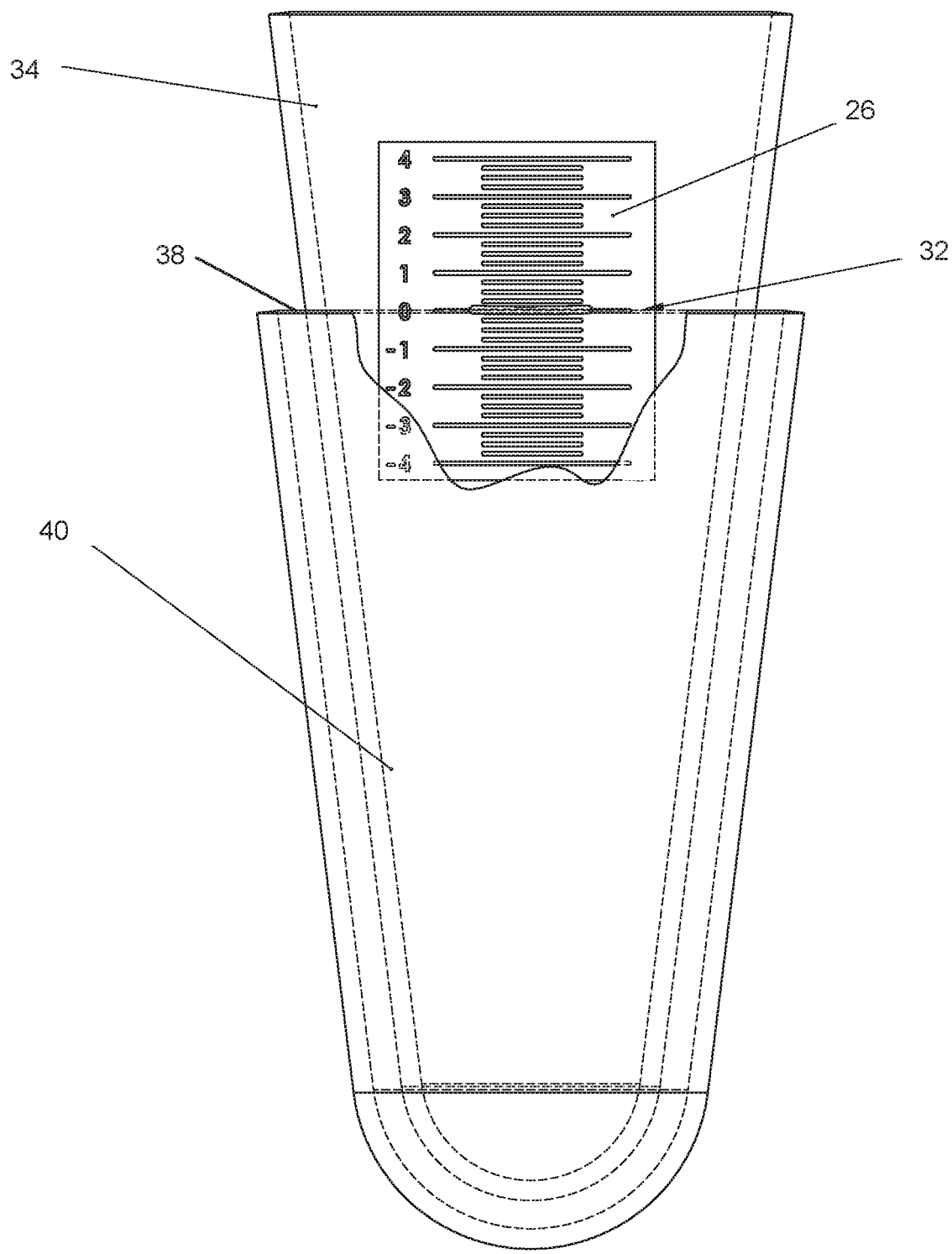
FIG. 6 is a view of the prosthetic sock of the present invention with the measuring template in place to show the "0" mark in line with the top edge of the prosthetic socket.

As seen in FIGS. 5 and 6, the measuring template 26 is put in place against the outer surface 34 of the prosthetic sock 10 and a baseline 36 is drawn where the zero mark 32 coincides with an upper edge 38 of a prosthetic socket 40 when the user is in a compressed stance. As the amputee uses the prosthetic sock 10 in combination with the prosthetic socket 40 and swelling or shrinkage occurs, the baseline 36 will move upwardly or downwardly accordingly. When the amputee notices the baseline 36 has moved sufficiently far enough away from its original placement, the amputee can use the measuring template 26 to determine how much volume the residual limb has gained or lost by virtue of measuring from the zero mark 32 to the height indicator 28 that coincides with the upper edge 38 of the prosthetic socket 40. Likewise, a prosthetist may do this measurement and tell the amputee what corrective measures should be taken. Alternatively, a mobile or online application can be programmed to periodically notify the user to check the level of the baseline 36, instruct the user to take appropriate corrective action after the user enters a status, inform the user of how many plies need to be added or removed depending on the type of prosthetic sock 10 being worn, and record the addition or removal of a sock. In addition, the application can be programmed to send an alarm to a user's prosthetist if the number of plies added or removed exceed a pre-established amount.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A system for volume management of a residual limb comprising:
   a measuring template further comprising a plurality of height indicators including a zero mark where the zero mark coincides with an upper edge of a prosthetic socket when the user is in a compressed stance forming a baseline and wherein the baseline shifts upwardly or downwardly based on swelling or shrinkage of an amputated limb;
   a tapered prosthetic sock having a distal end and a proximal end wherein the proximal end has a thickness between 0.4 to 1.0 millimeters and the distal end has a thickness between 1.2 and 1.8 millimeters, wherein the measuring template is separate from the tapered prosthetic sock.

2. A system for volume management of a residual limb comprising:
   a measuring template further comprising a plurality of height indicators including a zero mark where the zero mark coincides with an upper edge of a prosthetic socket when the user is in a compressed stance forming a baseline and wherein the baseline shifts upwardly or downwardly based on swelling or shrinkage of an amputated limb;
   a tapered prosthetic sock having a distal end and a proximal end wherein the distal end has a thickness between 0.4 and 1.0 millimeters and the proximal end has a thickness between 1.2 and 1.8 millimeters, wherein the measuring template is separate from the tapered prosthetic sock.

3. A system for volume management of a residual limb comprising:
   a measuring template further comprising a plurality of height indicators including a zero mark where the zero mark coincides with an upper edge of a prosthetic socket when the user is in a compressed stance forming a baseline and wherein the baseline shifts upwardly or downwardly based on swelling or shrinkage of an amputated limb;
a tapered prosthetic sock having a distal end and a proximal end wherein the tapered prosthetic sock tapers inward from the proximal end towards a medial section and then tapers outwardly towards the distal end and wherein medial section has a thickness between 1.2 and 1.8 millimeters and wherein the proximal end has a thickness between 0.4 and 1.0 millimeters, wherein the measuring template is a separate piece from the tapered prosthetic sock.

\* \* \* \* \*